United States Patent [19]

Kinzer

[11] Patent Number: 5,238,618
[45] Date of Patent: Aug. 24, 1993

[54] METHOD FOR PREPARING ORIENTED MICROPOROUS FILM

[75] Inventor: Kevin E. Kinzer, Cottage Grove, Minn.

[73] Assignee: Minnesota Mining and Manufacturing Company, St. Paul, Minn.

[21] Appl. No.: 754,277

[22] Filed: Aug. 30, 1991

Related U.S. Application Data

[60] Continuation of Ser. No. 374,488, Jun. 29, 1989, abandoned, which is a division of Ser. No. 98,601, Sep. 14, 1987, Pat. No. 4,867,881.

[51] Int. Cl.$^5$ .............................................. B29C 67/20
[52] U.S. Cl. ........................................ 264/41; 264/154; 264/204; 264/210.7; 264/235.6; 264/288.8; 264/290.2; 264/344
[58] Field of Search .............. 264/41, 154, 204, 210.1, 264/210.7, 210.8, 211.12, 233, 235.6, 235.8, 288.8, 290.2, 344

[56] References Cited

U.S. PATENT DOCUMENTS

| | | |
|---|---|---|
| 3,709,774 | 1/1973 | Kimura ............................ 210/490 |
| 4,220,543 | 9/1980 | Yamashita ...................... 210/500.36 |
| 4,377,616 | 3/1983 | Ashcraft et al. ................ 428/315.9 |
| 4,466,931 | 8/1984 | Tanny ................................. 264/49 |
| 4,490,431 | 12/1984 | Vitzthum ............................ 264/41 |
| 4,612,148 | 9/1986 | Motooka et al. ................ 264/210.6 |
| 4,774,039 | 9/1988 | Urasiolo ............................. 264/41 |

*Primary Examiner*—Leo B. Tentoni
*Attorney, Agent, or Firm*—Gary L. Griswold; Walter N. Kirn; Carole Truesdale

[57] ABSTRACT

A method for preparing an oriented microporous shaped article is provided. The method comprises the steps of melt blending thermoplastic polymer with a solubilizing amount of a compatible liquid to form a homogeneous solution, forming a shaped article from the solution, cooling the shaped article at a rate and to a temperature sufficient to initiate thermodynamic, non-equilibrium liquid-liquid phase separation and then to solidify the thermoplastic polymer, stretching the article in a first direction sufficient to permanently attenuate the article and effect orientation of the polymer, and removing at least a substantial portion of the compatible liquid before or after the stretching step to form an oriented microporous shaped article.

14 Claims, 10 Drawing Sheets

METHOD FOR PREPARING ORIENTED MICROPOROUS FILM

This is a continuation of application Ser. No. 07/374,488 filed Jun. 29, 1989, now abandoned, which is a division of application Ser. No. 07/098,601, filed Sep. 14, 1987, now U.S. Pat. No. 4,867,881.

FIELD OF THE INVENTION

The invention relates to microporous materials, a method of making microporous materials, and articles made therewith.

BACKGROUND OF THE INVENTION

Microporous films or membranes have a structure that enables fluids to flow through them. The effective pore size is at least several times the mean free path of the flowing molecules, namely from several micrometers down to about 100 Angstroms. Such sheets are generally opaque, even when made of a transparent material, because the surfaces and the internal structure scatter visible light. The term "microporous film" as used herein is inclusive of microporous membranes.

Microporous films have been utilized in a wide variety of applications such as for the filtration of solids, the ultrafiltration of colloidal matter, as diffusion barriers or separators in electrochemical cells, and in the preparation of synthetic leather, or cloth laminates. The latter utilities require, of course, permeability to water vapor but not liquid water for applications such as synthetic shoes, raincoats, outer wear, camping equipment such as tents, and the like. Microporous films are also utilized for filter cleaning antibiotics, beer, oils, bacteriological broths, as well as for the analysis of air, microbiological samples, intravenous fluids, vaccines and the like. Microporous films are also utilized to make surgical dressings, bandages, and in other fluid transmissive medical applications. The microporous film may be laminated to other articles to make laminates having particular utility. Such laminations may include a microporous layer and an outer shell layer to provide a particularly useful garment material. The microprous films or membranes may be utilized as a tape backing to provide products such as a vapor-transmissive wound dressing or hair set tape.

The art of preparing microporous structures is replete with a wide variety of methods of producing such articles. The formation of microporous polymeric membranes can be broadly classified into two general areas. The first class involves some modifications of a dense film to render it microporous. Methods commonly used to provide microporous films or membranes by dense film modifications are described in the following references:

U.S. Pat. No. 3,309,841 (Egleston et al.) describes the irradiation of a film to produce narrow trails or tracks of radiation-damaged material which can be etched with suitable reagents leaving cylindrical pores. Various patents assigned to W. L. Gore and Associates, Inc., including U.S. Pat. Nos. 3,953,566 (Gore); 3,962,153 (Gore); 4,096,227 (Gore); 4,110,392 (Yamazaki); 4,187,390 (Gore) and 4,194,041 (Gore et al.) describe the preparation of porous articles, including microporous sheets formed exclusively of polytetrafluoroethylene (PTFE), not a normally melt processable thermoplastic polymer, characterized by having polymer nodes connected by fibrils. Such articles are produced by extruding a paste comprised of PTFE particles and a lubricant, removing the lubricant and stretching and annealing the resultant product. The resultant product is a sintered, oriented porous film of PTFE.

U.S. Pat. Nos. 4,100,238 and 4,197,148 (Shinomura) describe the preparation of permeable membranes by kneading in the molten state two different kinds of thermoplastic synthetic resins which are partly compatible with each other, fabricating the molten mixture into a sheet, film or hollow articles, treating the fabricated article with a solvent which is a good solvent for one of the component resins but is a poor solvent for the other to dissolve and remove the former resin, drying the fabricated articles, and then stretching it. In place of the resin to be removed by the solvent, rubbers or oligomers having partial compatibility with the resin which remains undissolved can be used.

U.S. Pat. No. 3,679,540 (Zimmerman et al.) discloses a method for making open-celled microporous polymer film from non-porous, crystalline, elastic polymer starting film by cold stretching elastic polymer starting film until porous surface regions which are elongated normal or perpendicular to the stretch direction are formed, hot stretching the cold stretched film until fibrils and pores or open cells which are elongated parallel to the stretch direction are formed and then heat setting the resultant porous film. Generally, controlled porosity is difficult to attain in such films because they do not always uniformly fibrillate to a specific pore size.

U.S. Pat. No. 4,206,980 (Krueger et al.) discloses normally transparent films which can be rendered translucent by stretching and transparent by relaxing the film. The films are a blend of crystallizable polymer with a compound with which the polymer is miscible at a temperature above the crystallization temperature of the crystallizable polymer-compound blend but immiscible at a temperature below the crystallization temperature of the blend. The films are prepared by blending the crystallizable polymer with the compound under melt conditions, casting a film of the blend and cooling to solidify the blend. The film cannot be stretched beyond its elastic limit, as is normally done during orientation, as this would cause permanent deformation and a loss of the transparent/translucent properties.

Certain U.S. patents disclose the preparation of porous polymer films by blending into the polymer a non-miscible leachable particulate substance such as starch, salts, etc. forming a sheet and leaching the particulate substance from the polymer sheet. Such U.S. patents include U.S. Pat. Nos. 3,214,501 (Strauss) and 3,640,829 (Elton). U.S. Pat. No. 3,870,593 (Elton et al.) discloses the preparation of a porous, preferably microporous polymer sheet by blending non-miscible, non-leachable filler into the polymer, forming a sheet of the blend and stretching the sheet to form pores which are initiated at the sites of the filler particles.

The second class of microporous polymeric membrans are those which result from a phase separation phenomenon. The phase separation can be that of a liquid-liquid or a liquid-solid nature. The formation of microporous membranes through chemically induced liquid-liquid phase separation, commonly called phase inversion, has been commercially utilized to form microporous polymers from cellulose acetate and certain other polymers. Generally these materials are not oriented but used as cast. Phase inversion has been reviewed in great detail by R. E. Kesting in "Synthetic Polymeric Membranes", 2nd Edition, John Wiley &

Sons, 1985. U.S. Pat. No. 4,482,514 (Schindler et al.) describes a process for the production of an ultrafiltration membrane from polyamide wherein the material is oriented. The process involves forming a membrane from a solution of polyamide in formic acid through phase inversion, preferably orienting the film by stretching 1.5:1 to 2.5:1 in the wet state drying the membrane, and, if oriented, heat setting the film.

Additional developments in microporous membrane fabrication by phase separation utilize thermally-induced phase separation. In thermally-induced phase separation, a component which is liquid at processing temperatures is combined with the polymer from which the membrane is to be formed. This liquid component is a non-solvent for the polymer at low temperatures but combines with the polymer to produce a homogeneous solution at an elevated temperature. Methods used to provide microporous films or membranes by the thermal process are described in the following references:

U.S. Pat. No. 4,564,488 (Gerlach et al.) discloses porous fibers and membranes prepared by forming a homogeneous mixture of at least two components, one of which is a meltable polymer and the other a liquid which is said to be inert with respect to the polymer. The mixture formed must be of a binary type, in which there is a temperature range of complete miscibility and a temperature range in which there is a miscibility gap. The mixture is extruded at a temperature above the separation temperature into a bath containing at least some of the inert liquid which is at a temperature below the separation temperature. Upon introduction of the mixture into the bath, the fiber or membrane structure of the product is fixed. The fibers or membranes are characterized by a smooth porous surface and an apparent density of between about 10 and 90% of the true density of the polymeric starting material employed.

U.S. Pat. Nos. 4,247,498 and 4,519,909 (Castro) disclose microporous polymers in forms ranging from films to blocks and intricate shapes from synthetic thermoplastic polymers, such as olefinic, condensation, and oxidation polymers. The microporous polymers are characterized by a relatively homogeneous, three-dimensional cellular structure having cells connected by pores of smaller dimension. The microporous polymers are made from such thermoplastic polymers by heating a mixture of the polymer and a compatible liquid to form a homogeneous solution, cooling the solution under non-equilibrium thermodynamic conditions to initiate liquid-liquid phase separation, and continuing cooling until the mixture achieves substantial handling strength. The microporous polymer products may contain relatively large amounts of functionally useful liquids and behave as solids. These microporous polymers must be made under specified temperature/concentration conditions and are not oriented.

U.S. Pat. No. 4,539,256 (Shipman) discloses an oriented article having a microporous structure characterized by a multiplicity of spaced randomly dispersed, equiaxed, non-uniform shaped particles of a crystallizable thermoplastic polymer which are coated with a compound which is miscible with the thermoplastic polymer at the melting temperature of the polymer but phase separates on cooling at or below the crystallization temperature of the polymer. Adjacent thermoplastic particles within the article are connected to each other by a plurality of fibrils consisting of the thermoplastic polymer. The fibrils radiate in three dimensions from each particle. The compound may be removed from the sheet article. The microporous structure is made by melt-blending the polymer with the compound, forming a shaped article of the melt blend, cooling the shaped article to a temperature at which the polymer crystallized to cause liquid-solid phase separation to occur between the thermoplastic polymer and the compound, and orienting the resultant structure in at least one direction to provide the article.

Although useful microporous films and membranes are provided by the above-described disclosures, a need has been felt for microporous films and membranes which have uniform microporosity as well as a substantially extended range of useful properties and improved control over those properties.

SUMMARY OF THE INVENTION

The present invention relates to a microporous article which comprises a thermoplastic polymeric structure having a plurality of cells with adjacent cells being interconnected by passageways to provide a network of communicating pores and the structure being oriented in at least one direction. The thermoplastic polymeric structure may be substantially homogeneous or the porosity of the structure may be gradient therethrough. The cells comprise void spaces encased by fibrous, lacy, or semi-continuous boundaries. The cells are generally ellipsoidal in shape with an aspect ratio of major axis to minor axis greater than 1.0 and a major axis generally lying in a plane parallel to the surface of the article. The matrix tensile strength at break in the oriented direction is preferably increased at least 10% over an unoriented structure. The microporous article preferably has a porosity greater than 25%, a thickness of less than 1000 μm, and a maximum effective pore diameter of from about 0.01 to 10 microns.

The present invention also relates to an article which comprises a sheet material having a thermoplastic polymeric structure having a microporous structure with a plurality of cells with adjacent cells being interconnected by passageways to provide a network of communicating pores extending to one major surface of said sheet material and a non-microporous structure at an opposite major surface of said sheet material and a non-microporous structure at an opposite major surface of said sheet material.

The present invention further relates to a method for preparing a microporous thermoplastic polymeric shaped article which comprises the steps of a) melt blending thermoplastic polymer with a solubilizing amount of a compatible liquid to form a homogeneous solution;

b) forming an article from the solution;

c) cooling the shaped article at a rate and to a temperature sufficient to initiate thermodynamic, non-equilibrium liquid-liquid phase separation;

d) further cooling the article to solidify the thermoplastic polymer;

e) stretching the article in at least one direction sufficient to permanently attenuate the article and effect orientation of the polymer; and f) removing at least a substantial portion of the compatible liquid before or after the stretching step.

The process of the invention provides microporous articles, such as films, fibers, hollow fibers, and tubes, with a network of communicating pores, greater effective pore size range, reduced fluid flow resistance, improved pore size control and enhanced mechanical strength. Thin, microporous films having greater porosity and void volume than previously attainable with liquid-liquid phase separation techniques can be easily produced. The films of the invention are thinner and have greater mechanical strength for a given pore size than previous microporous films produced by liquid-liquid phase separation. Microporous films with comparable effective pore size can be produced with higher polymer concentrations in the melt and at lower temperatures than with previous liquid-liquid phase separation techniques.

DETAILED DESCRIPTION OF THE INVENTION

Figure 1:
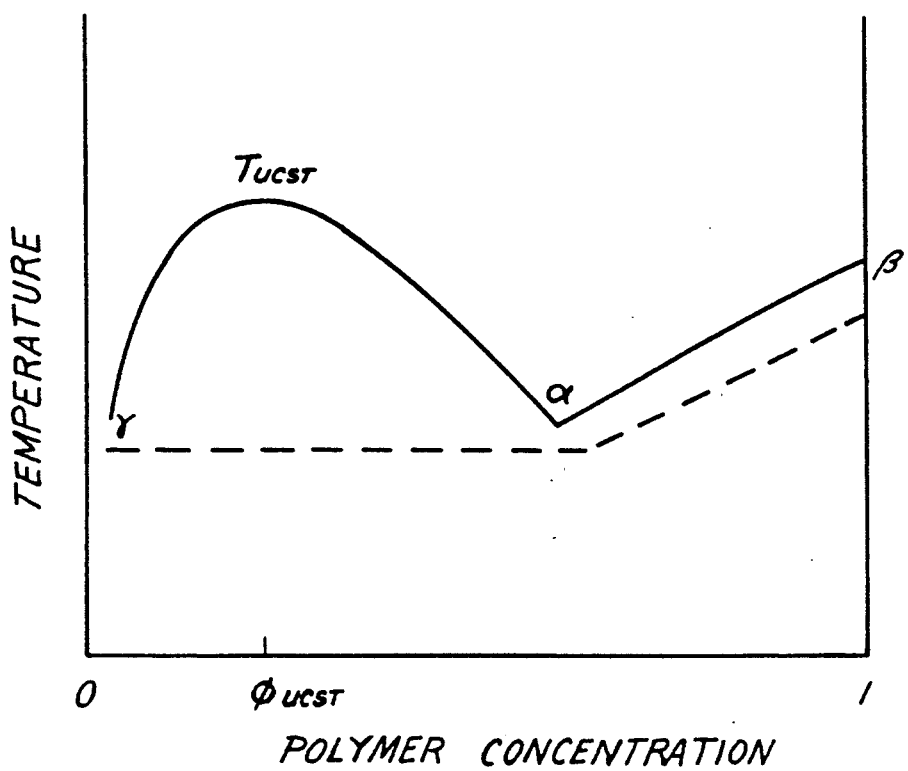
FIG. 1 is a temperature-composition plot for a thermoplastic polymer/compatible liquid system of the invention.

As used herein, the term "thermoplastic polymer" refers only to conventional polymers, both crystalline and non-crystalline, which are melt processable under ordinary melt processing conditions and does not include polymers such as polytetrafluoroethylene which, under extreme conditions, may be thermoplastic and melt-processable.

As used herein, the term "crystalline", as used with regard to the thermoplastic polymer, includes polymers which are at least partially crystalline. Crystalline polymer structures in melt-processed thermoplastic polymers are well-known.

As used herein, the term "amorphous", as used with regard to the thermoplastic polymer, includes polymers without substantial crystalline ordering such as, for example, polymethylmethacrylate, polysulfone, and atactic polystyrene.

As used herein, the term "melting temperature" refers to the temperature at which the thermoplastic polymer, in a blend of thermoplastic polymer and compatible liquid, will melt.

As used herein, the term "crystallization temperature" refers to temperature at which the thermoplastic polymer, in a melt blend of thermoplastic polymer and compatible liquid, will crystallize.

As used herein, the term "equilibrium melting point", as used with regard to the thermoplastic polymer, refers to the commonly accepted melting point temperature of the thermoplastic polymer as found in published literature.

Thermoplastic polymers useful in the present invention include olefinic, condensation and oxidation polymers. Representative olefinic polymers include high and low density polyethylene, polypropylene, polyvinyl-containing polymers, butadiene-containing polymers and acrylate-containing polymers such as polymethylmethacrylate. Condensation polymers include polyesters such as polyethylene terephthalate and polybutylene terephthalate, polyamides such as nylon 6, nylon 11, nylon 13 and nylon 66, polycarbonates and polysulfones. Polyphenylene oxide is representative of the oxidation polymers which can be used. Blends of thermoplastic polymers may also be used.

The compatible liquid is a material which is capable of forming a solution with the thermoplastic polymer when heated above the melt temperature of the polymer and which phase separates from the polymer by liquid-liquid phase separation, rather than liquid-solid phase separation, on cooling. The compatibility of the liquid with the polymer can be determined by heating the polymer and the liquid to form a clear homogeneous solution. If a solution of the polymer and the liquid cannot be formed at any liquid concentration, then the liquid is inappropriate for use with that polymer. In practice, the liquid used may include compounds which are solid a room temperature but liquid at the melt temperature of the polymer. The operability of a specific liquid with a given polymer cannot be predicted with absolute certainty. However, certain guidelines can be set forth. For non-polar polymers, non-polar organic liquids with similar room temperature solubility parameters are generally useful at the solution temperatures. Similarly, polar organic liquids are generally useful with polar polymers. When blends of polymers are used, useful liquids are those which are compatible liquids for each of the polymers used. When the polymer is a block copolymer such as styrene-butadiene, the liquid selected must be compatible with each type of polymer block. Blends of two or more liquids can be used as the compatible liquid as long as the selected polymer is soluble in the liquid blend at the polymer melt temperature and the solution formed separates by liquid-liquid phase separation on cooling.

Various types of organic compounds have been found useful as the compatible liquid, including aliphatic and aromatic acids, aliphatic, aromatic and cyclic alcohols, aldehydes, primary and secondary amines, aromatic and ethoxylated amines, diamines, amides, esters and diesters, ethers, ketones and various hydrocarbons and heterocyclics. When the polymer selected is polypropylene, esters such as dibutyl phthalate and ethers such as dibenzyl ether are useful as the compatible liquid. When high density polyethylene is the polymer, an aliphatic ketone such as methyl nonyl ketone or an ester such as dioctyl phthalate are useful as the compatible liquid. Compatible liquids for use with low density polyethylene include aliphatic acids such as decanoic acid and oleic acid or primary alcohols such as decyl alcohol. When the polymer selected is nylon 11, esters such as propylene carbonate, ethylene carbonate, or tetramethylene sulfone are useful as the compatible liquid. When the polymer selected is polymethylmethacrylate, useful compatible liquids include, 1,4-butanediol and lauric acid. A compatible liquid for use with the polymer polyphenylene oxide is, for example, tallowamine.

The relative amounts of thermoplastic polymer and compatible liquid vary with each system. The polymer concentration which can be used in a given system can be determined by reference to the temperature-compositions diagrams for that system. A general temperature-composition graph for a semi-crystalline polymer-liquid systems is set forth in FIG. 1. Such graphs can be readily developed by known techniques such as that set forth in Smolders, van Aartsen and Steenbergen, Kolloid-Z.u.Z. Polymere, 243, 14–20 (1971).

The portion of the curve from gamma to alpha represents the thermodynamic equilibrium liquid-liquid phase separation. $T_{UCST}$ represents the upper critical solution temperature, i.e., the maximum temperature of the system at which liquid-liquid phase separation will occur. $\Phi_{UCST}$ represents the critical composition. To form the microporous polymers of the present invention, the polymer concentration utilized for a particular system must be greater than $\Phi_{UCST}$. If the polymer concentration is less than $\Phi_{UCST}$, the phase separation which occurs as the system is cooled forms a continuous liquid phase with a discontinuous polymer phase, resulting in a structure which cannot be oriented. The portion of the curve from alpha to beta represents equilibrium liquid-solid phase separation. The dashed line represents the crystallization temperature-concentration relationship and shows the lowering of the crystallization temperature as a consequence of cooling at a rate sufficient to achieve thermodynamic non-equilibrium phase separation. The flat portion of the crystallization temperature-concentration curve at polymer concentrations greater than $\Phi_{UCST}$ defines the useful concentration range which is a function of the cooling rate employed. For a given cooling rate in a system, the crystallization temperature-concentration curve of the compatible liquid can be determined and from this curve the concentration ranges for the polymer and the liquid which will yield the desired microporous structure at the given cooling rate can be determined. The determination of the crystallization curve is an alternative to determining the temperature-concentration phase diagram for a system incorporating a semicrystalline polymer.

The actual polymer concentration selected from within the predetermined concentration range for the liquid-polymer system being used is limited by functional considerations. The polymer concentration should be sufficient to provide the microporous structure which is formed on cooling with adequate strength for handleability in further processing steps. The polymer concentration should be such that the viscosity of the liquid-polymer melt solution is suitable for the equipment used to shape the article. Generally, the polymer concentration in the compatible liquid is about 10 to 75 weight percent.

Figure 2:
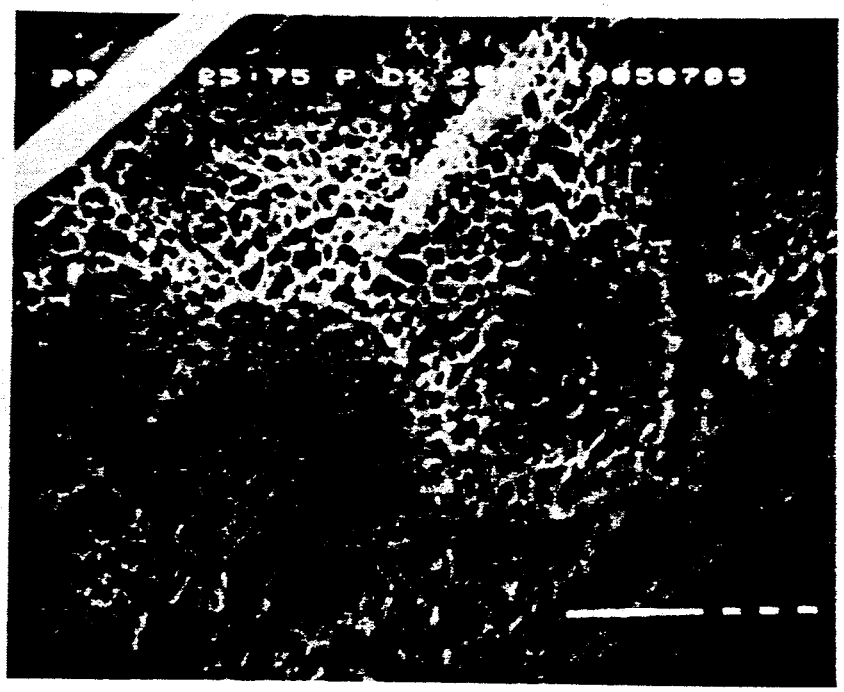
FIG. 2 is a scanning electron photomicrograph at 200× of a prior art unstretched film cooled at 1° C./min.
Figure 3:
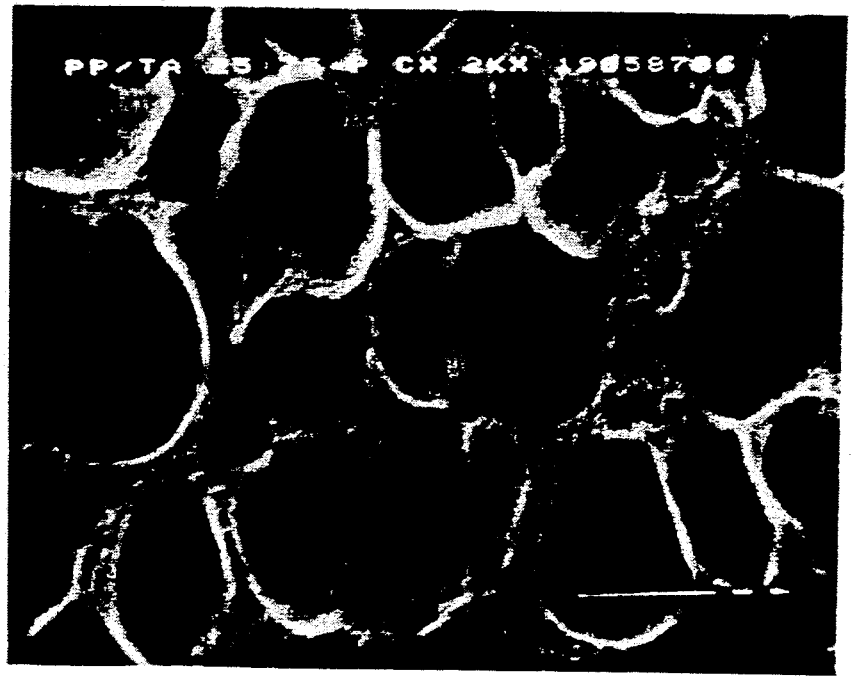
FIG. 3 is a scanning electron photomicrograph of a portion of the prior art unstretched film shown in FIG. 2 at 2000×.
Figure 4:
FIG. 4 is a scanning electron photomicrograph at 200× of a prior art unstretched film cooled at 1700° C./min.
Figure 5:
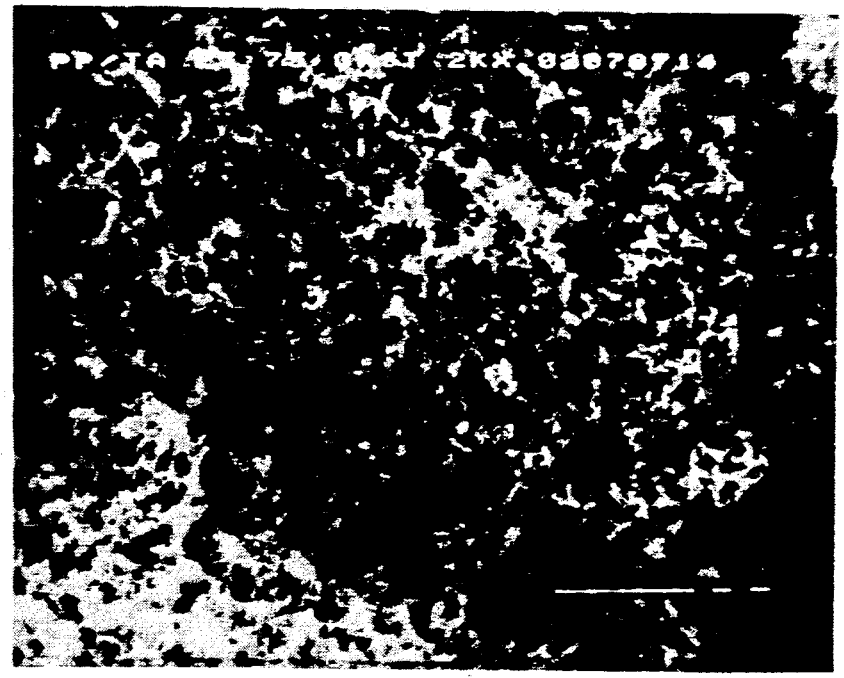
FIG. 5 is a scanning electron photomicrograph of a portion of the prior art unstretched film shown in FIG. 4 at 2000×.

In the process of the present invention, the rate of cooling of the solution may be varied within wide limits as long as the rate is sufficient that the liquid-liquid phase separation does not occur under thermodynamic equilibrium conditions. For many liquid-polymer systems, when the rate of cooling of the liquid-polymer solution is slow, but sufficient to result in liquid-liquid phase separation, liquid-liquid phase separation occurs at substantially the same time as the formation of a plurality of liquid droplets of substantially uniform size. When the cooling rate is such that the droplets form, the resultant microporous polymer will have the desired cellular microstructure. If the rate of cooling of the liquid-polymer solution is rapid, the solution undergoes a spontaneous transformation called spinodal decomposition, the resultant microporous polymer will have a fine open-cellular microstructure. This fine microporous structure is referred to as a lacy structure. FIGS. 2 through 5 demonstrate types of structures which can be produced by non-equilibrium liquid-liquid phase separation. FIGS. 2 and 3 are cross-sectional views of an unoriented microporous membrane prepared by cooling a 25 weight percent polypropylene solution in tallowamine from 200° C. to 25° C. at a slow rate, i.e., 1° C./min. The resulting structure is termed "open cellular." FIGS. 4 and 5 are cross-sectional views of the same unoriented polymer solution rapidly quenched, i.e., at a rate of 1700° C./min, from 200° C. to 25° C. The structure obtained is termed a "lacy" structure. Thus, for a given liquid-polymer system, differing microporous structures can be obtained by varying the cooling rate.

The microporous structures of this invention are oriented, i.e., stretched beyond their elastic limit to introduce permanent set or elongation and to ensure that the micropores are permanently developed or formed. This orientation of the microporous structures aids in controlling pore size and enhances both the porosity and the mechanical properties of the material. Prior to orientation, the microporous structure is a relatively homogenous cellular or sponge-like structure of substantially spherical microcells distributed substantially uniformly throughout the structure. After orientation, the microcells tend to have a substantially ellipsoidal shape.

Orientation causes the microporous structure to expand such that the porosity increases while the pore size remains relatively unchanged. The combination of high porosity and small pore size is particularly desirable in filtration applications. Orientation can be used as a process variable to control thickness and relatively thin microporous films can be produced. Thickness is particularly important for microporous film applications where selective transport through the microporous film is desired, since the rate of transport is inversely proportional to the thickness. Decreasing thickness minimizes the hydrostatic resistance to flow through the film. Orientation enables production of thin films with minimal difficulty. Orientation also enhances the mechanical strength of the films which is beneficial in virtually all microporous film applications. With increasing orientation, film thickness, and resistance to flow, are proportionately reduced, mechanical strength, porosity, and pore size are proportionately increased, and the pore size range is extended with improved pore size control, so that an excellent balance of desired properties can be attained through selection of the amount of orientation to which the microporous film is subjected.

The microporous structures may be uniaxially or biaxially oriented. Preferably, the microporous structures are stretched at least about 10 percent, more preferably about 10 to 1000 percent. The actual amount of stretching required is dependent upon the particular composition of the article and the degree of porosity desired. Stretching of the structure is preferably uniform so that the oriented structure has uniform, controlled porosity. When the structures are uniaxially oriented, narrowing of the structure in the non-oriented direction generally occurs, such that stretching a structure, for example, a film, 50 percent does not result in a 50 percent increase in surface area, but something less than a 50 percent increase. The orientation is preferably dimensionally stabilized in the material using well-known techniques such as, for example, heating the material to a stabilizing temperature under restraint.

Figure 6:
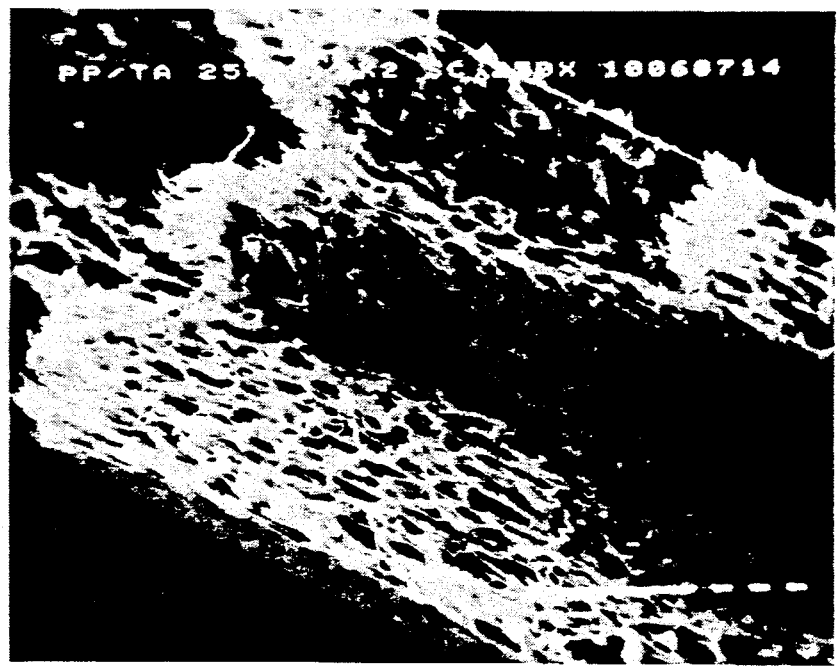
FIG. 6 is a scanning electron photomicrograph at 250× of the film of FIG. 2 after stretching 2×2, a film of the present invention.
Figure 7:
FIG. 7 is a scanning electron photomicrograph of a portion of the film of the present invention shown in FIG. 6 at 2000×.
Figure 8:
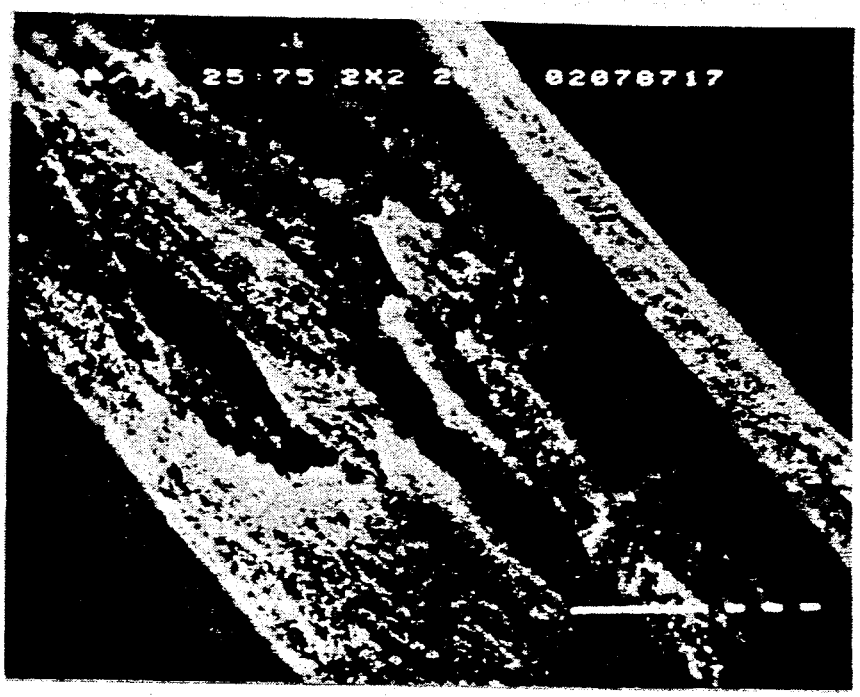
FIG. 8 is a scanning electron photomicrograph at 200× of the film of FIG. 4 after stretching 2×2, a film of the present invention.
Figure 9:
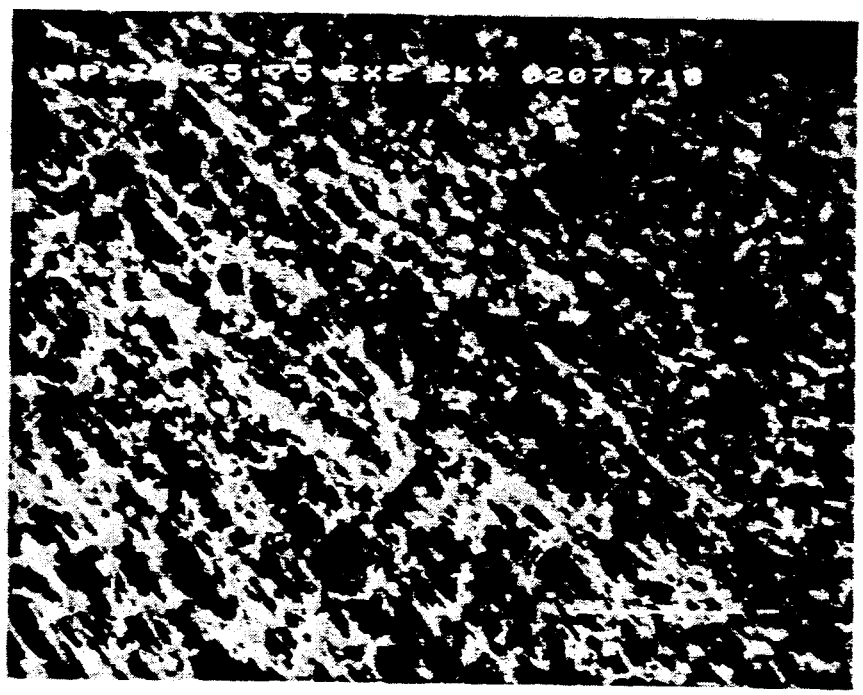
FIG. 9 is a scanning electron photomicrograph of a portion of the film of the present invention shown in FIG. 8 at 2000×.

FIGS. 2 and 3 are scanning electron photomicrographs, at magnifications of 200× and 2000×, respectively, of the cellular structure obtained from liquid-liquid phase separation, in a system employing 25 weight percent polypropylene as the thermoplastic polymer and 75 weight percent tallowamine as the compatible liquid and cooled at 1° C./min. FIGS. 6 and 7 are scanning electron photomicrographs, at magnifications of 250× and 2000×, respectively, of the same material as shown in FIGS. 2 and 3 after orientation according to the present invention at a stretch ratio of 2:1 in both the machine and transverse directions. FIGS. 4 and 5 are scanning electron photomicrographs, at magnifications of 200× and 2000×, respectively, of the lacy structure obtained from liquid-liquid phase separation, in a system employing 25 weight percent polypropylene as the thermoplastic polymer and 75 weight percent tallowamine as the compatible liquid and a cooling rate of 1700° C./min. FIGS. 8 and 9 are scanning electron photomicrographs, at magnifications of 200× and 2000×, respectively, of the same material as shown in FIGS. 4 and 5 after orientation according to the present invention at a stretch ratio of 2:1 in both the machine and transverse directions. As can be seen, orientation causes expansion of the thermoplastic polymer in both the cellular and lacy structures which results in a more open porous structure than is achieved in the unoriented material. This greater porosity is particularly useful in filtration, diffusion barriers, and imbibing materials.

The compatible liquid may be removed from the microporous material either before or after orientation to yield a liquid-free microporous polymeric material. The compatible liquid can be removed by, for example, solvent extraction, volatilization, or any other convenient method. After removal of the compatible liquid, the resulting microporous material may be modified by imbibition of various materials, such as, for example, liquids, solvent solutions, solvent dispersions, or solids. Such materials may be imbibed by any of a number of known methods which result in the deposition of such materials within the porous structure of the microporous material. The imbibed material may be physically entrapped within the microporous structure or chemically reacted with the polymeric material which forms the microporous structure. Examples of imbibing materials include medicaments, fragrances, antistatic agents, surfactants, pesticides and solid particulate material such as activated carbon and pigments. Certain materials, such as antistatic agents and surfactants, may be imbibed without removal of the compatible liquid.

The microporous material of the invention may be further modified, either before or after removal of the compatible liquid, by depositing various materials on the surface thereof using known coating or deposition techniques. For example, the microporous material may be coated with metal by vapor deposition or sputtering techniques or materials such as adhesives, aqueous or solvent-based compositions, and dyes can be coated on the microporous material. Coating can be accomplished by such conventional coating techniques as, for example, roller coating, spray coating, dip coating, and the like.

Microporous sheet materials of the invention may be laminated to various other materials such as, for example, woven, knitted, or nonwoven fabrics, films, or to one or more additional layers of microporous sheet material to achieve, for example desired porosity gradients, handling properties, and aesthetics. Lamination can be carried out using conventional techniques such as adhesive bonding, spot welding, or other techniques which do not undesirably interfere with the porosity or create undesirable porosity or perforations.

Figure 10:
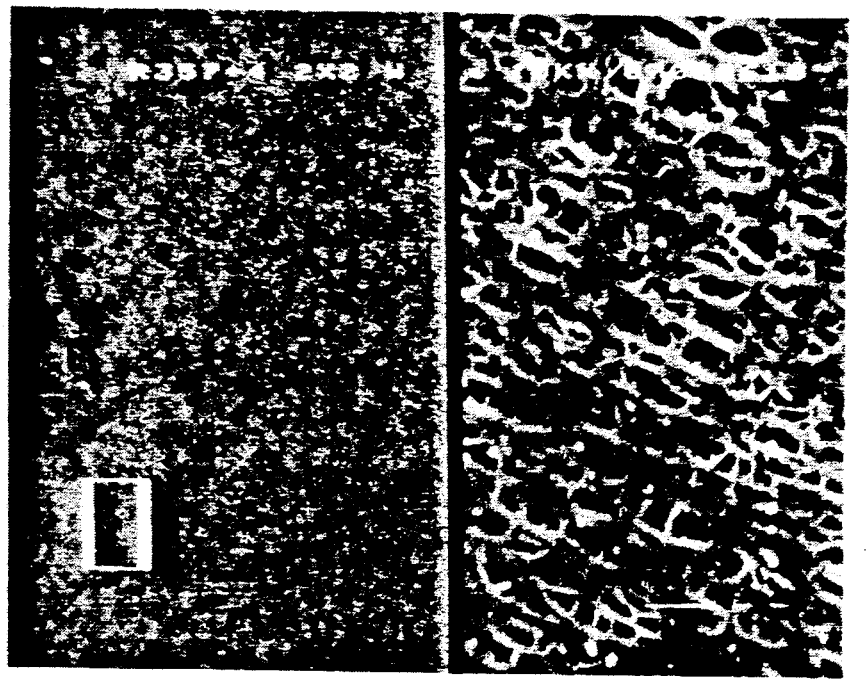
FIG. 10 is a split image scanning electron photomicrograph (1000×/10,000×) of the surface of the film of Example 14 which was in contact with the casting wheel.
Figure 11:
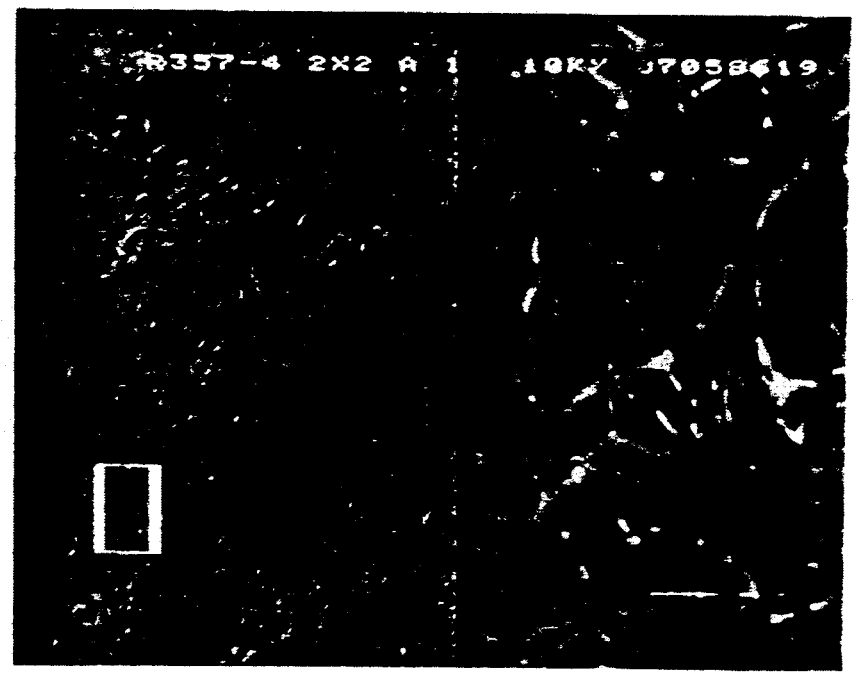
FIG. 11 is a split image scanning electron photomicrograph (1000×/10,000×) of the surface of the film of Example 14 which was not in contact with the casting wheel.

The microporous material of the invention may be modified to produce a porous membrane having a gradient porosity therethrough, if the extruded film is rapidly cooled from one surface thereof, such as by bringing the surface into contact with a chilled casting wheel. The surface of the film in contact with, for example, the chilled casting wheel can be fused or sealed, while the opposite side remains porous. Orientation of this gradient porosity structure enhances the porosity differences from surface to surface. FIGS. 10 and 11 are split image scanning electron photomicrographs at magnifications of 1000× and 10,000× of the surface structure obtained by casting a solution of 41 weight percent polypropylene in tallowamine onto a 60° C. casting wheel at a thickness of 170 μm and orienting at a stretch ratio of 2:1 in both the machine and transverse directions after removal of the tallowamine. The film surface cast in contact with the casting wheel is shown in FIG. 10, while the surface not in direct contact with the casting wheel is shown in FIG. 11. Films with such properties can be used, for example, for microfiltration or ultrafiltration or as protective films or tapes, having, for example, the porous side readily markable and the sealed side resistant to marking.

The microporous materials of the invention are useful in a variety of applications where microporosity is desirable. For example, the microporous sheet materials can be used for ultrafiltration of colloidal matter, as filtering material for cleaning antibiotics, beer, oils, and bacteriological broths, and as diffusion barriers or separators in electrochemical cells. The microporous sheet material can also be used for sample collection in air analysis and for collection of microbiological specimens. When laminated to woven or knitted fabric or to nonwoven fabric such as a nonwoven scrim material, the microporous materials can be useful for outerwear such as rainwear, camping equipment such as tents and sleeping bags, and for disposable protective garments for use, for example, in hospitals, electronic clean rooms, or in areas where contact with hazardous chemicals can occur. The microporous sheet materials are also useful in surgical dressings, bandages, and other medical applications.

The following examples further illustrate this invention, but the particular materials and amounts thereof in these examples, as well as other conditions and details, should not be construed to unduly limit this invention. In the examples, all parts and percentages are by weight unless otherwise specified. Where stretch ratios are recited for extruded films, the first number indicates the stretch ratio in the machine direction (MD), i.e., extrusion direction, and the second number indicates the stretch ratio in the direction transverse to the extrusion direction (TD).

In the Examples, the following test methods were used in evaluating the various films:

| | |
|---|---|
| Gurley Value: | This value is a measurement of time in seconds to pass 50 cc of air through a film according to ASTM D-726 Method A. |
| Maximum Effective Pore Diameter: | This value is measured in microns according to ASTM F-316 and is termed pore diameter in the Examples. |
| Bulk Density: | This value is determined from measurement of specific gravity according to ASTM D-792. |
| Porosity: | A calculated value based on the measured bulk density and polymer density using the following equation: $$\text{Porosity} = \left(1 - \frac{\text{bulk density}}{\text{polymer density}}\right) \times 100$$ |
| Bulk Tensile: | Measured values according to ASTM D-882 using an Instron model 1122 under the following conditions: Jaw gap: 2 in Jaw speed: 20 in/min Sample size: 1-in wide strip |
| Matrix Tensile: | Calculated value based on the bulk tensile strength and porosity according to the following equation: $$\text{Matrix Tensile} = \frac{100}{100 - \text{Porosity}} \times \text{Bulk Tensile}$$ |

EXAMPLES 1-10 AND COMPARATIVE EXAMPLES C1-C4

High density polyethylene, HDPE, (American Hoechst GM 9255), a thermoplastic polymer, and dioctyl phthalate, DOP, a liquid compatible with the HPDE, were melt blended to form homogeneous mixtures at the ratios and temperatures set forth in Table 1. Each blend was extruded at a rate of 18 kg/hr using a twin screw extruder with a screw speed of 150 rpm, a film die having a slot 0.05 cm wide and 30.5 cm long, and a line speed as set forth in Table 1. The extruded film was cooled in a water quench bath 1 cm from the die at the bath temperature set forth in Table 1 to initiate thermodynamic, non-equilibrium liquid-liquid phase separation and solidification of the film. The thickness of each film was measured and is set forth in Table 1.

TABLE 1

| Film | HDPE:DOP | Melt temp (°C.) | Line speed (m/min) | Bath temp (°C.) | Thickness (μm) |
|---|---|---|---|---|---|
| A | 39:61 | 252 | 10.0 | 32 | 120 |
| B | 49:51 | 269 | 9.1 | 40 | 125 |
| C | 40:60 | 267 | 8.8 | 37 | 117 |
| D | 34:66 | 263 | 8.8 | 37 | 122 |

Samples of each film were restrained in a frame and washed with 1,1,1-trichloroethane to remove the dioctyl phthalate. The restrained, washed films were dried to remove any residual 1,1,1-trichloroethane. In Examples 1-10, samples of each film were oriented by stretching at a temperature of 77° C., a preheat time of about 30 seconds, a stretch rate of 2.54 cm/sec, and the stretch ratios set forth in Table 2. While maintained at this stretch ratio, the oriented films were then heat set at a temperature of 93° C. The resulting microporous films and comparative non-oriented films were evaluated for thickness, Gurley value, pore diameter, porosity, and matrix tensile properties. The results are set forth in Table 2.

TABLE 2

| Example | Film | Stretch ratio | Thickness (μm) | Gurley value (S/50 cc) | Pore Diameter (μm) | Porosity (%) | Elongation @ break (%) MD | Elongation @ break (%) TD | Matrix tensile @ break (kPa) MD | Matrix tensile @ break (kPa) TD |
|---|---|---|---|---|---|---|---|---|---|---|
| C1 | A | none | 114 | 434.3 | 0.15 | 51.6 | 928 | 1020 | 26610 | 23650 |
| 1 | A | 1.5 × 1.5 | 89 | 47.6 | 0.20 | 68.3 | 489 | 210 | 33190 | 28620 |
| 2 | A | 2.5 × 2.5 | 43 | 17.6 | 0.19 | 83.9 | 68 | 155 | 65650 | 65560 |
| 3 | A | 3.5 × 3.5 | 25 | 14.9 | 0.14 | 86.3 | 71 | 79 | 103430 | 122600 |
| C2 | B | none | 124 | 3356.0 | 0.15 | 39.8 | 782 | 1239 | 25840 | 24770 |
| 4 | B | 2.5 × 2.5 | 48 | 29.9 | 0.20 | 75.4 | 106 | 72 | 53730 | 53510 |
| C3 | C | none | 117 | 496.6 | 0.14 | 50.2 | 863 | 1116 | 21970 | 21530 |
| 5 | C | 2.5 × 2.5 | 66 | 19.4 | 0.23 | 83.4 | 111 | 157 | 43490 | 45940 |
| 6 | C | 1.5 × 1 | 109 | 119.9 | 0.17 | 57.8 | 758 | 881 | 26270 | 20720 |
| 7 | C | 2.5 × 1 | 76 | 44.5 | 0.22 | 69.7 | 160 | 882 | 47130 | 13470 |
| 8 | C | 3.5 × 1 | 76 | 41.1 | 0.22 | 74.8 | 112 | 883 | 65530 | 13050 |
| C4 | D | none | 122 | 158.3 | 0.17 | 59.6 | 443 | 641 | 13620 | 14680 |
| 9 | D | 2.5 × 2.5 | 71 | 13.0 | 0.21 | 87.5 | 119 | 54 | 30280 | 44020 |
| 10 | D | 3.5 × 3.5 | 25 | 8.8 | 0.22 | 89.3 | 61 | 56 | 60510 | 86730 |

As can be seen from the data in Table 2, a broad range of properties can be obtained by varying the film composition and the stretch conditions under which the film is oriented. The data demonstrates that generally as the degree of orientation increases, the thickness decreases, the Gurley value decreases significantly, and the pore diameter, porosity, and matrix tensile properties increase. Such a modification in properties, attained by orientation, allows for much greater control over film properties than was previously achievable with films prepared by liquid-liquid phase separation.

EXAMPLE 11-14 AND COMPARATIVE EXAMPLES C5-C8

Polypropylene, PP, (Exxon TM 3014, available from Exxon Corp., or Profax TM 6723, available from Himont, Inc., as indicated in Table 3) and tallowamine, TA, (Armostat TM 310, available from Armak Chemical Co.) were melt blended to form homogeneous mixtures at the ratios and temperatures set forth in Table 3. Each blend was extruded at a rate of approximately 3 kg/hr using a 2.54 cm diameter single screw extruder and a film die having a slot 0.05 cm wide and 15.2 cm long at a line speed of 2.1 m/min. The extruded film was cooled on a 60° C. casting wheel to initiate thermodynamic, non-equilibrium liquid-liquid phase separation and solidification of the film. The thickness of each film was measured and is set forth in Table 3.

TABLE 3

| Film | PP resin | PP:TA ratio | Melt temp (°C.) | Thickness (μm) |
|---|---|---|---|---|
| E | Exxon 3014 | 61:39 | 250 | 117 |
| F | Profax 6723 | 61:39 | 250 | 124 |
| G | Profax 6723 | 51:49 | 260 | 170 |
| H | Profax 6723 | 41:59 | 261 | 170 |

Samples of each film were restrained in a frame and washed with 1,1,1-trichloroethane to remove the tallowamine. The restrained, washed films were dried to remove any residual 1,1,1-trichloroethane. In Examples 11-14, samples of each film were oriented by stretching at a temperature of 121° C., a preheat time of about 1 minute, a stretch rate of 1.27 cm/sec, and a stretch ratio of 2×2. The resulting microporous films and comparative non-oriented films were evaluated for thickness, Gurley value, pore diameter, porosity, and matrix tensile properties. The results are set forth in Table 4.

conditions under which the film is oriented. The data demonstrate that the oriented films of this invention have reduced thickness, significantly decreased Gurley value, and increased pore diameter, porosity, and matrix tensile properties over the non-oriented film alone.

EXAMPLES 15-21 AND COMPARATIVE EXAMPLES C9-C14

Polypropylene (Profax TM, available from Himont, Inc.) was melt blended with tallowamine, TA, (Examples 15-21 and Comparative Example C9) or with white mineral oil, MO, (Comparative Examples C10-C14) at polypropylene:compatible liquid ratios of 57:43 and a temperature of 246° C. to form homogeneous mixtures. Each blend was extruded at a rate of about 3 kg/hr using a 2.54 cm diameter single screw extruder and a film die having a slot 0.05 cm wide and 15.2 cm long, at a line speed of 2.1 m/min, onto a 43° C. casting wheel to form films 160 μm thick. Cooling of the polypropylene-tallowamine blend initiated thermodynamic, non-equilibrium, liquid-liquid phase separation and solidification of the film. Cooling of the polypropylene-mineral oil blend initiated thermodynamic, non-equilibrium, liquid-solid phase separation and solidification of the film.

Samples of each film were restrained in a frame and washed with 1,1,1-trichloroethane to remove the compatible liquid. The restrained, washed films were dried to remove any residual 1,1,1-trichloroethane. For examples 15-21 and Comparative Examples C11-C14, the films were oriented by stretching at a temperature of 121° C., a preheat time of 1 minute, a stretch rate of 1.27 cm/sec, and the stretch ratios set forth in Table 5. Attempts to stretch the film which was made using mineral oil as the compatible liquid were unsuccessful at stretch ratios greater than 2×2 due to mechanical failure of the samples. The various films were evaluated for thickness, Gurley value, pore diameter, porosity and

TABLE 4

| Example | Film | Stretch ratio | Thickness (μm) | Gurley value (S/50 cc) | Pore Diameter (μm) | Porosity (%) | Elongation @ break (%) MD | Elongation @ break (%) TD | Matrix tensile @ break (kPa) MD | Matrix tensile @ break (kPa) TD |
|---|---|---|---|---|---|---|---|---|---|---|
| C5 | E | none | 114 | 5000 | 0.087 | 37.4 | 506 | 589 | 24410 | 22650 |
| 11 | E | 2 × 2 | 69 | 41 | 0.193 | 74.0 | 134 | 108 | 62600 | 52200 |
| C6 | F | none | 117 | 4369 | 0.070 | 26.1 | 341 | 926 | 29120 | 33280 |
| 12 | F | 2 × 2 | 61 | 111 | 0.100 | 61.1 | 36 | 191 | 66870 | 57010 |
| C7 | G | none | 168 | 743 | 0.095 | 44.6 | 174 | 705 | 21350 | 23540 |
| 13 | G | 2 × 2 | 97 | 44 | 0.142 | 75.3 | 20 | 226 | 41610 | 57440 |
| C8 | H | none | 168 | 211 | 0.140 | 54.4 | 169 | 614 | 18340 | 20290 |
| 14 | H | 2 × 2 | 99 | 21 | 0.203 | 81.1 | 13 | 160 | 31280 | 52350 |

As can be seen from the data in Tables 3 and 4, a broad range of properties can be obtained by varying the polymers, the film compositions, and the stretch matrix tensile properties. The results are set forth in Table 5.

TABLE 5

| Ex. | Compatible Liquid | Stretch ratio | Thickness (μm) | Gurley value (S/50 cc) | Pore Diameter (μm) | Porosity (%) | Elongation @ break (%) MD | Elongation @ break (%) TD | Matrix tensile @ break (kPa) MD | Matrix tensile @ break (kPa) TD |
|---|---|---|---|---|---|---|---|---|---|---|
| C9 | TA | none | 158 | 3680 | 0.050 | 34.4 | 315 | 677 | 29050 | 24630 |
| 15 | TA | 1.5 × 1 | 121 | 1538 | 0.063 | 34.1 | 39 | 243 | 58030 | 22640 |
| 16 | TA | 1.5 × 1.5 | 99 | 272 | 0.086 | 47.4 | 111 | 261 | 54280 | 43860 |
| 17 | TA | 2.0 × 1 | 102 | 939 | 0.064 | 35.3 | 54 | 592 | 81580 | 26030 |
| 18 | TA | 2.0 × 2.0 | 74 | 159 | 0.085 | 54.1 | 63 | 113 | 69720 | 51610 |
| 19 | TA | 2.5 × 2.5 | 51 | 122 | 0.081 | 60.1 | 38 | 64 | 90350 | 67140 |
| 20 | TA | 3.0 × 3.0 | 40 | 71 | 0.082 | 63.5 | 24 | 20 | 81510 | 48770 |
| 21 | TA | 3.5 × 3.0 | 37 | 69 | 0.076 | 68.6 | 20 | 45 | 88250 | 84490 |
| C10 | MO | none | 127 | 8249 | 0.083 | 2.1 | 11 | 8 | 4430 | 850 |
| C11 | MO | 1.5 × 1 | 122 | 446 | 0.343 | 5.0 | 12 | 8 | 25010 | 12740 |

TABLE 5-continued

| Ex. | Compatible Liquid | Stretch ratio | Thickness (μm) | Gurley value (S/50 cc) | Pore Diameter (μm) | Porosity (%) | Elongation @ break (%) MD | Elongation @ break (%) TD | Matrix tensile @ break (kPa) MD | Matrix tensile @ break (kPa) TD |
|---|---|---|---|---|---|---|---|---|---|---|
| C12 | MO | 1.5 × 1.5 | 83 | 105 | 0.556 | 11.6 | 10 | 13 | 16030 | 22000 |
| C13 | MO | 2.0 × 1 | 79 | 163 | 0.518 | 7.5 | 10 | 9 | 22780 | 12120 |
| C14 | MO | 2.0 × 2.0 | 65 | 48 | 0.960 | 24.2 | 8 | 9 | 11110 | 17310 |

As can be seen from the data in Table 5, a broad range of properties can be obtained by varying the stretch ratio under which the liquid-liquid phase separated film is oriented. The data demonstrate that, in the films of this invention, as the degree of orientation increases, the thickness decreases, the Gurley value decreases significantly, and the porosity and matrix tensile properties increase, while the maximum effective pore diameter remains relatively constant and that the prior art films are significantly weaker, have larger pore size, i.e., maximum effective pore diameter, and lower porosity.

Figure 12:
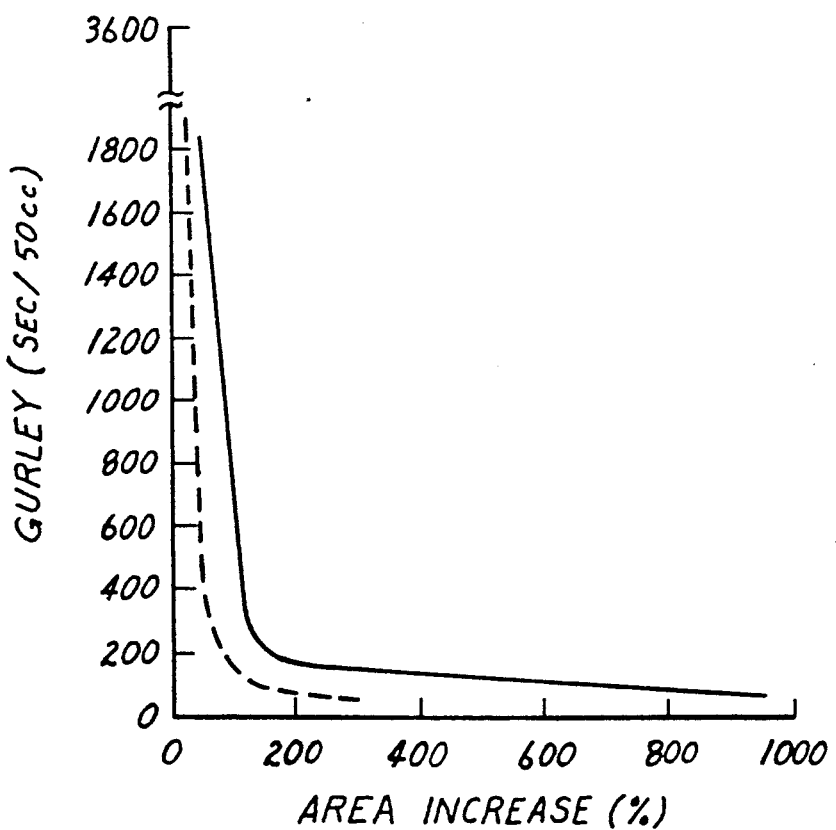
FIG. 12 illustrates the effect of stretching a microporous polypropylene film on air flow through the film.
Figure 13:
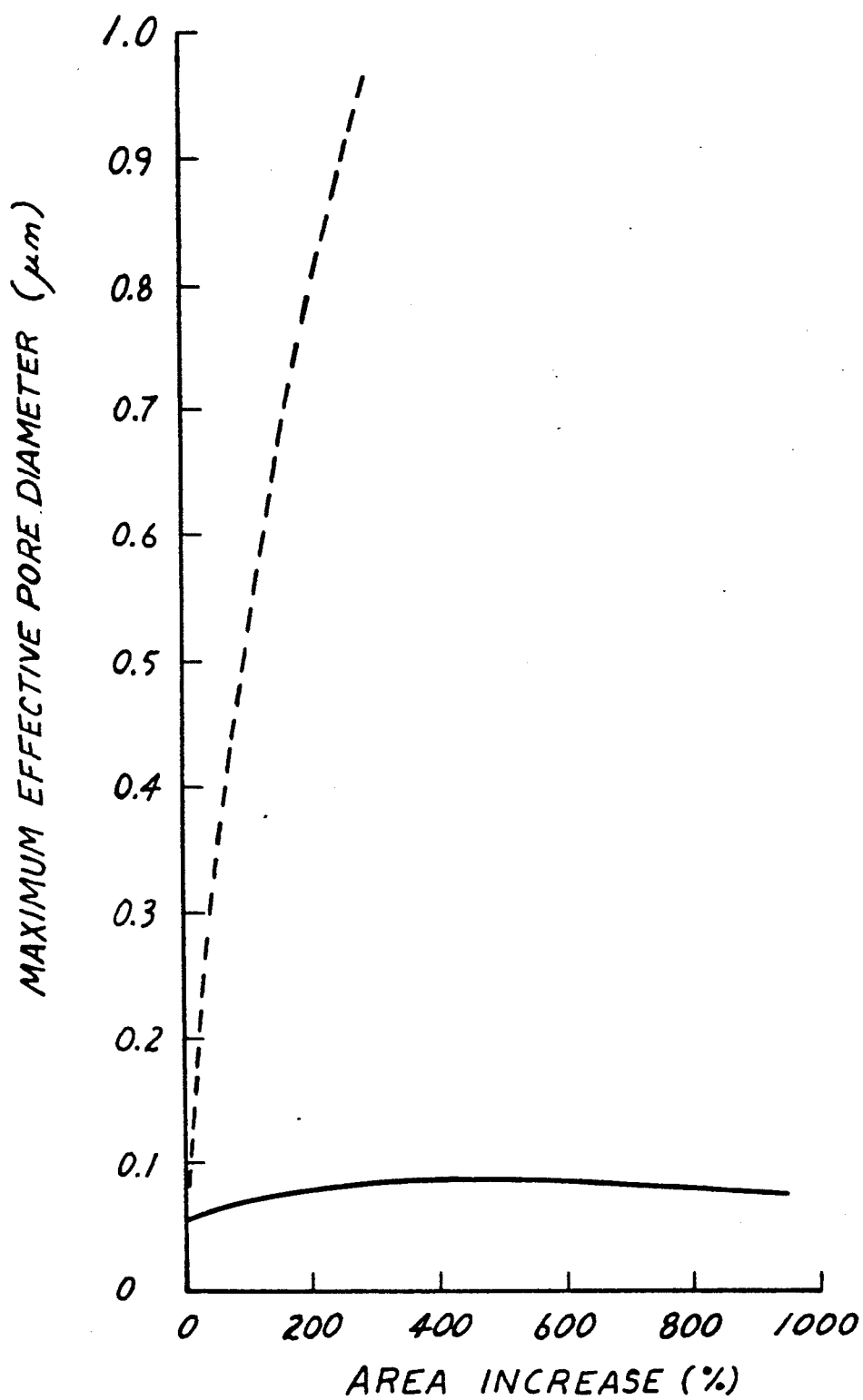
FIG. 13 illustrates the effect of stretching a microporous polypropylene film on the maximum effective pore diameter of the film.
Figure 14:
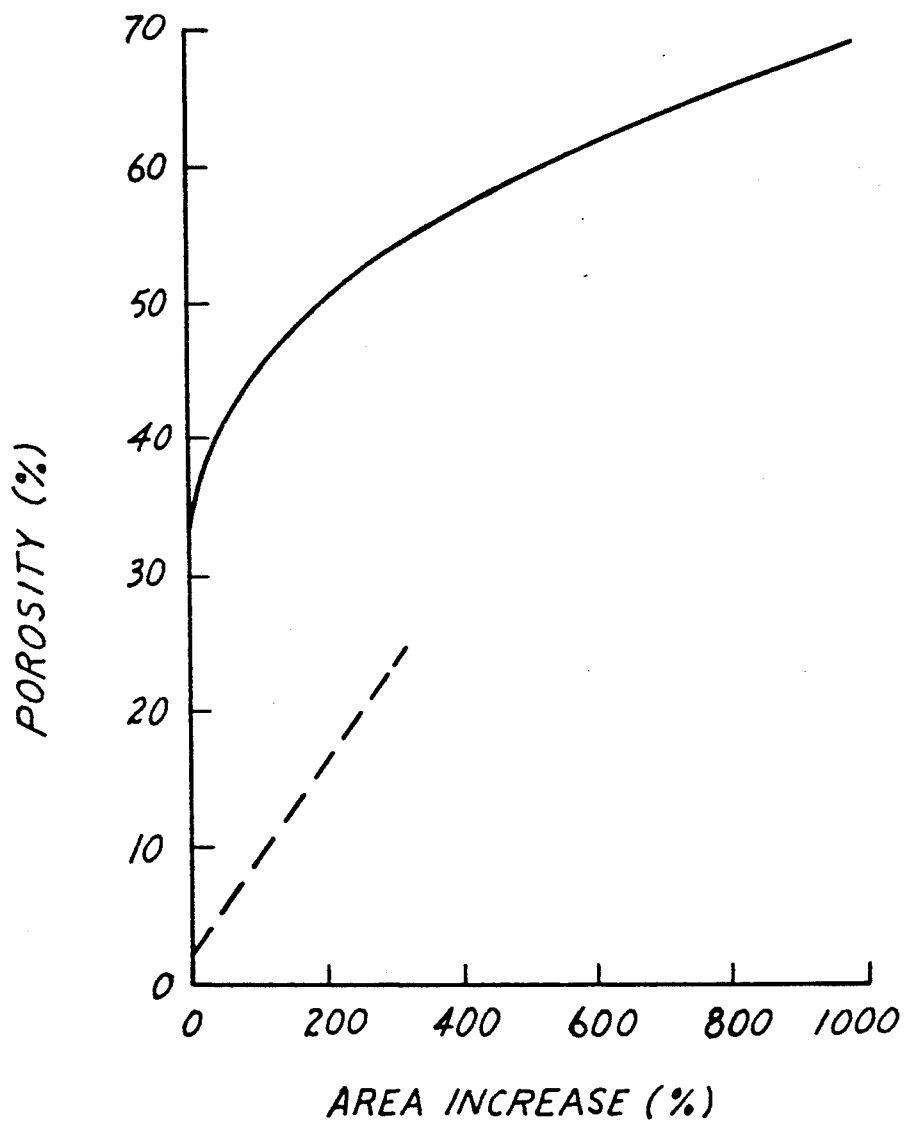
FIG. 14 illustrates the effect of stretching a microporous polypropylene film on the porosity of the film.

In FIGS. 12-14, the Gurley value, pore diameter, and porosity, respectively, are plotted against the area increase (machine direction stretch ratio x transverse direction stretch ratio) for the film of the invention (solid line) prepared from the liquid-liquid phase separated polypropylene and tallowamine and a prior art film (broken line) prepared from liquid-solid phase separated polypropylene and mineral oil. These FIGS. emphasize the relatively constant pore diameter and increased porosity attainable in films of the present invention as compared to the prior art films.

EXAMPLES 22 AND 23 AND COMPARATIVE EXAMPLES C15 AND C16

A blend of 25 parts polypropylene (Profax TM 6723, available from Himont, Inc.) and 75 parts tallowamine (Armostat TM 310, available from Armak Co.) were batch-mixed for 3 hours at 200° C. under a nitrogen atmosphere to form a homogeneous solution. In Example 22 and Comparative Example C15, portions of the solution were pressed between plates heated to 175° C. to form films about 0.5 mm thick and the plates were allowed to cool at approximately 1° C./min. For Example 23 and Comparative Example C16, portions of the solution were pressed between plates heated to 175° C. to form a film about 0.5 mm thick and the plates were immersed into a 20° C. water bath to effect a cooling rate of about 1700° C./min.

Each film was restrained in a frame and washed with 1,1,1-trichloroethane to remove the tallowamine. The restrained, washed films were dried to remove any residual 1,1,1-trichloroethane. The films of Examples 22 and 23 were oriented by stretching at a temperature of 121° C., a preheat time of about 1 minute, a stretch ratio of 1.27 cm/sec, and a stretch ratio of 2×2. The resulting oriented microporous films and comparative non-oriented films were examined by scanning electron microscopy and photomicrographs were taken of the films. The film of Comparative Example 15, FIGS. 2 and 3, exhibits an open-cellular structure, while the film of Comparative Example 16, FIGS. 4 and 5, exhibits a lacy structure. The films were also evaluated for thickness, Gurley value, pore diameter, density, and porosity. The results are set forth in Table 6.

TABLE 6

| Example | Cooling rate (°C./min) | Stretch ratio | Thickness (μm) | Gurley value (S/50 cc) | Pore Diameter (μm) | Bulk density (g/cc) | Porosity (%) |
|---|---|---|---|---|---|---|---|
| C15 | 1 | none | 460 | 694 | 0.39 | 0.245 | 72.9 |
| 22 | 1 | 2 × 2 | 320 | 2 | 9.25 | 0.134 | 85.1 |
| C16 | 1700 | none | 510 | 185 | 0.42 | 0.277 | 69.2 |
| 23 | 1700 | 2 × 2 | 380 | 11.5 | 1.02 | 0.099 | 89.0 |

As can be seen from the data in Table 6, the oriented film cooled at a rate of 1700° C./min. has a higher Gurley value, a smaller pore diameter and bulk density, and higher porosity than the oriented film cooled at a rate of 1° C./min.

EXAMPLE 24 AND COMPARATIVE EXAMPLE C17 and C18

In Comparative Example C17, a blend of 10 parts polypropylene, available from Exxon Corp. under the trade designation "3014", and 90 parts tallowamine, available from Armak Chemical Co. as Armostat TM 310, were batch mixed for 3 hours at 200° C. under a nitrogen atmosphere. The blend formed a homogeneous solution which was pressed between plates heated to 180° C. to form a film approximately 0.5 mm thick which was then quenched in a 5° C. water bath. The resulting film had little physical integrity and tore under its own weight.

In Example 24 and Comparative Example C18, film was prepared as in Comparative Example C17 except that a blend of 15 parts of polypropylene and 85 parts tallowamine were used. The resulting film was extracted with 1,1,1-trichloroethane to remove the tallowamine and then dried in air under restraint. A sample of the film was stretched 2×2 at 121° C. (Example 24) and evaluated, together with an unstretched sample of film (Comparative Example C18), for thickness, Gurley value, pore diameter, bulk density, and porosity. The results are set forth in Table 7.

TABLE 7

|  | Comparative Example C18 | Example 24 |
|---|---|---|
| Thickness (μm): | 675 | 405 |
| Gurley value (sec/50 cc): | 19.8 | 2.6 |
| Pore Diameter (μm): | 1.03 | 1.74 |
| Bulk density (g/cc): | 0.379 | 0.074 |
| Porosity (%): | 57.9 | 91.8 |

As can be seen from the data in Table 7, the stretched film of Example 24 had a significant improvement in Gurley value and reduction in bulk density, as well as an increase in pore diameter and porosity. Orientation of the film produced from a lower compatible liquid concentration (85% in Comparative Example C18 as compared to 90% in Comparative Example C17) permitted fabrication of a film with higher porosity (91.8%, Example 24) than can be achieved by merely increasing the compatible liquid concentration.

EXAMPLES 25-33 AND COMPARATIVE EXAMPLE C19

A commercially available liquid-liquid phase separated microporous polypropylene film, Accurel TM available from Enka America, Inc., having a nominal pore size of 0.1 micrometer, was oriented at stretch temperatures and stretch ratios set forth in Table 8, with a preheat time of 60 seconds, and a stretch rate of 1.25 cm/sec. The resulting microporous films and the comparative non-oriented Accurel TM film were evaluated for thickness, Gurley value, pore diameter, porosity, and matrix tensile properties. The results are set forth in Table 8.

pore diameter, porosity, and matrix tensile values were increased.

EXAMPLE 38 AND COMPARATIVE EXAMPLE C21

A blend of 30 parts nylon 11, a thermoplastic condensation polymer available from Aldrich Chemicals as catalog number "18,115-3", and 70 parts propylene carbonate, a compatible liquid available from Aldrich Chemicals, were batch mixed for 3 hours at 215° C. under a nitrogen atmosphere. The blend formed a homogeneous solution which was pressed between plates heated to 190° C. to form a film approximately 0.5 mm thick which was then quenched in a 5° C. water bath. The sheets were then extracted in 1,1,1-trichloroethane to remove the propylene carbonate and then dried in air under restraint. The resulting film was stretched 2×2 at 121° C. (Example 38) and evaluated, together with an

TABLE 8

| Example | Stretch ratio | Stretch Temp (°C.) | Thickness (μm) | Gurley value (S/50 cc) | Pore Diameter (μm) | Porosity (%) | Elongation @ break (%) | | Matrix tensile @ break (kPa) | |
|---|---|---|---|---|---|---|---|---|---|---|
| | | | | | | | MD | TD | MD | TD |
| C19 | none | — | 97 | 31.8 | 0.26 | 69.0 | 86 | 92 | 7550 | 7130 |
| 25 | 1.25 × 1 | 120 | 94 | 22.7 | 0.34 | 71.2 | 58 | 62 | 8820 | 5870 |
| 26 | 1.25 × 1.25 | 120 | 86 | 12.9 | 0.40 | 76.2 | 27 | 34 | 7440 | 8700 |
| 27 | 1.5 × 1 | 120 | 86 | 13.1 | 0.38 | 73.6 | 35 | 64 | 10230 | 5380 |
| 28 | 1.5 × 1.5 | 120 | 79 | 6.2 | 0.46 | 81.4 | 17 | 25 | 7040 | 9570 |
| 29 | 2 × 1 | 120 | 86 | 11.2 | 0.38 | 80.5 | 12 | 36 | 16100 | 4620 |
| 30 | 2 × 2 | 120 | 66 | 4.5 | 0.49 | 88.9 | 18 | 9 | 8830 | 10270 |
| 31 | 2 × 2 | 138 | 64 | 4.2 | 0.50 | 86.9 | 10 | 8 | 17480 | 23820 |
| 32 | 2.5 × 1 | 138 | 74 | 7.5 | 0.45 | 82.1 | 10 | 48 | 38490 | 8550 |
| 33 | 2.5 × 2 | 128 | 53 | 3.4 | 0.52 | 89.8 | 9 | 17 | 25490 | 22750 |

As can be seen from the data in Table 8, orienting the film reduced the thickness and Gurley value, while the pore diameter, porosity, and matrix tensile values were increased. Examples 30 and 31 demonstrate the increase in matrix tensile properties attainable by increasing the stretch temperature. The thickness, Gurley value, pore diameter, and porosity of the films of Examples 30 and 31 were substantially similar.

EXAMPLES 34-37 AND COMPARATIVE EXAMPLE C20

A commercially available liquid-liquid phase separated microporous polypropylene film, Accurel TM available from Enka America, Inc., having a nominal pore size of 0.2 micrometer, was oriented at a stretch temperature of 120° C., with a preheat time of 60 seconds, a stretch rate of 1.25 cm/sec, and the stretch ratios set forth in Table 9. The resulting microporous films and the comparative non-oriented Accurel TM film were evaluated for thickness, Gurley value, pore diameter, porosity, and matrix tensile properties. The results are set forth in Table 9.

unstretched sample of film (Comparative Example C21) for thickness, Gurley value, pore diameter, bulk density, and porosity. The results are set forth in Table 10.

TABLE 10

| | Comparative Example C21 | Example 38 |
|---|---|---|
| Thickness (μm): | 880 | 530 |
| Gurley value (sec/50 cc): | no air flow | 4561 |
| Pore Diameter (μm): | not measurable | 0.30 |
| Bulk density (g/cc): | 0.979 | 0.318 |
| Porosity (%): | 11.0 | 71.1 |

As can be seen from the data in Table 10, the unstretched sheets had no measurable airflow, while the 2×2 stretched sheets had measurable airflow (4561 sec/50 cc Gurley value).

Figure 15:
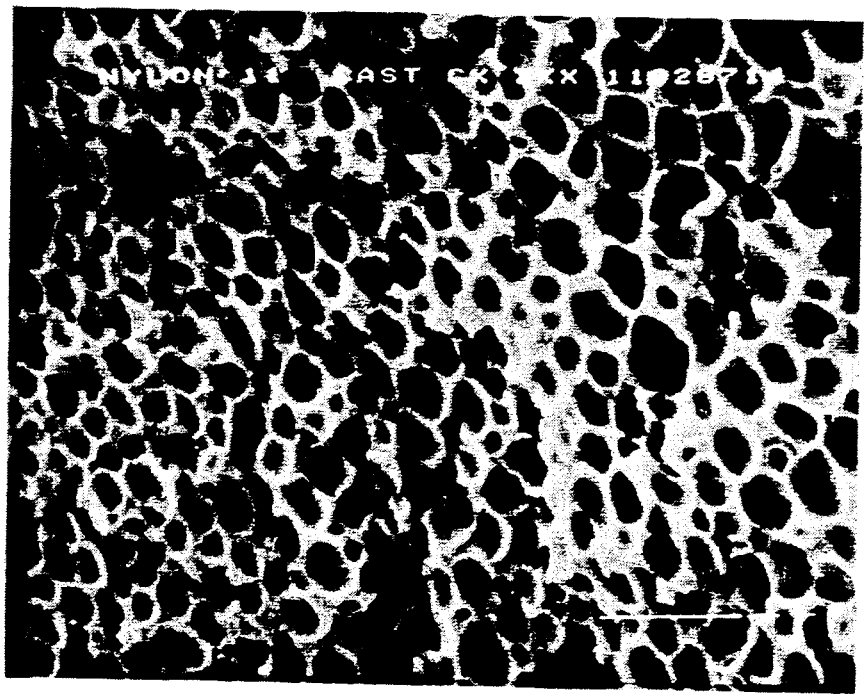
FIG. 15 is a scanning electron photomicrograph of the film of Comparative Example C21 at 2000×.

A photomicrograph of the unstretched film of Comparative Example C21 at 2000× magnification is shown in FIG. 15. Although this unstretched film has an open cellular structure, the lack of airflow indicates that the cells are not connected by pores throughout the thick-

TABLE 9

| Example | Stretch ratio | Thickness (μm) | Gurley value (S/50 cc) | Pore Diameter (μm) | Porosity (%) | Elongation @ break (%) | | Matrix tensile @ break (kPa) | |
|---|---|---|---|---|---|---|---|---|---|
| | | | | | | MD | TD | MD | TD |
| C20 | none | 147 | 23.9 | 0.52 | 71.7 | 41 | 65 | 8870 | 10780 |
| 34 | 1.25 × 1 | 137 | 12.4 | 0.66 | 75.2 | 32 | 40 | 12260 | 10560 |
| 35 | 1.25 × 1.25 | 130 | 10.0 | 0.83 | 79.8 | 12 | 18 | 10740 | 14060 |
| 36 | 1.5 × 1.5 | 122 | 5.8 | 1.03 | 84.3 | 7 | 10 | 9750 | 15920 |
| 37 | 2.0 × 2.0 | 109 | 4.2 | 1.12 | 89.6 | 15 | 1 | 11630 | 17120 |

Figure 16:
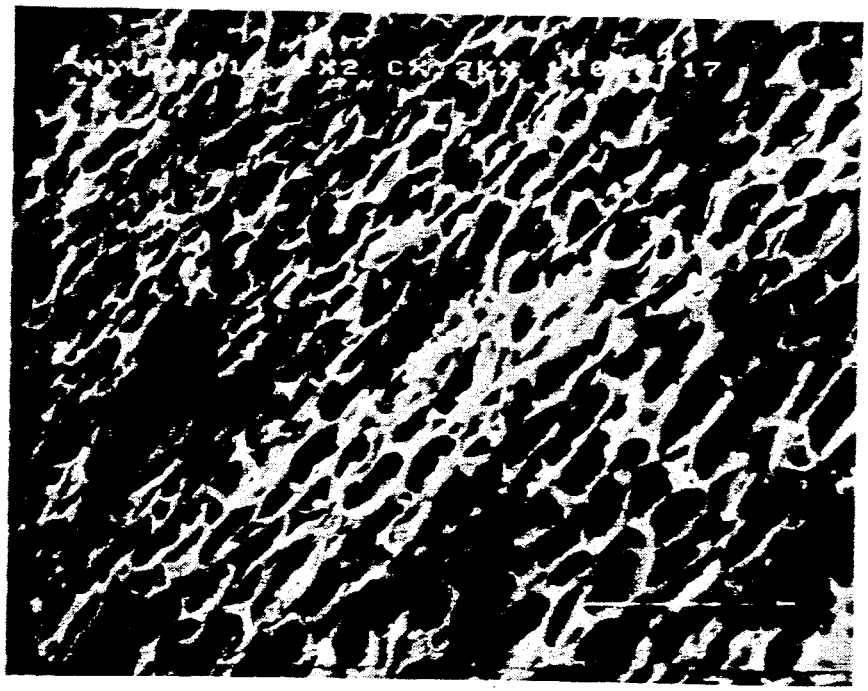
FIG. 16 is a scanning electron photomicrograph of the film of Example 38 at 2000×.

As can be seen from the data in Table 9, orienting the film reduced the thickness and Gurley value, while the ness of the film. A photomicrograph of the stretched film of Example 38 at 2000× magnification is shown in FIG. 16. This stretched film has ellipsoidal cells connected by pores. The pores are interconnected throughout the film as evidenced by the 4561 sec/50 cc Gurley value.

EXAMPLE 39 AND COMPARATIVE EXAMPLE C22

A blend of 30 parts polymethyl methacrylate, a non-crystalline amorphous thermoplastic polymer available from Rohm & Haas under the trade designation "V-811-100", and 70 parts 1,4-butanediol, a compatible liquid available from Aldrich Chemicals, were batch mixed for 3 hours at 200° C. under a nitrogen blanket. The blend formed a homogeneous solution which was pressed between plates heated to 180° C. to form a film approximately 0.5 mm thick which was then quenched in a 50° C. water bath. The film was then extracted with isopropyl alcohol to remove the 1,4-butanediol and then dried in air while being restrained. The resulting film was stretched 2×2 at 115° C. (Example 39) and evaluated, together with an unstretched sample of film, (Comparative Example C22) for thickness, Gurley value, pore diameter, bulk density, and porosity. The results are set forth in Table 6.

TABLE 11

|  | Comparative Example C22 | Example 39 |
| --- | --- | --- |
| Thickness (μm): | 710 | 140 |
| Gurley value (sec/50 cc): | no air flow | 137.1 |
| Pore Diameter (μm): | not measurable | 0.30 |
| Bulk Density (g/cc): | 0.843 | 0.462 |
| Porosity (%): | 28.6 | 60.9 |

Figure 17:
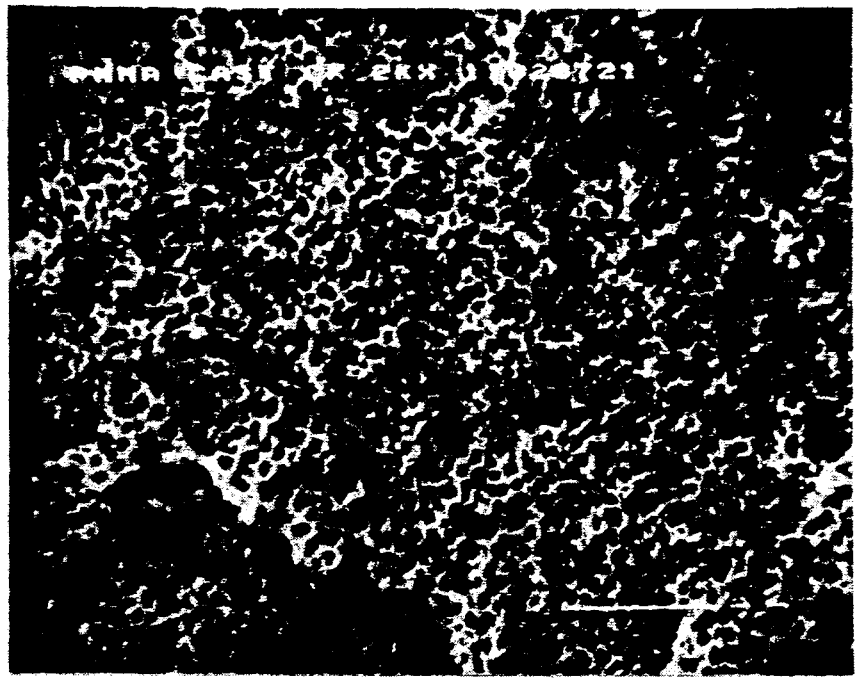
FIG. 17 is a scanning electron photomicrograph of the film of Comparative Example C22 at 2000×.
Figure 18:
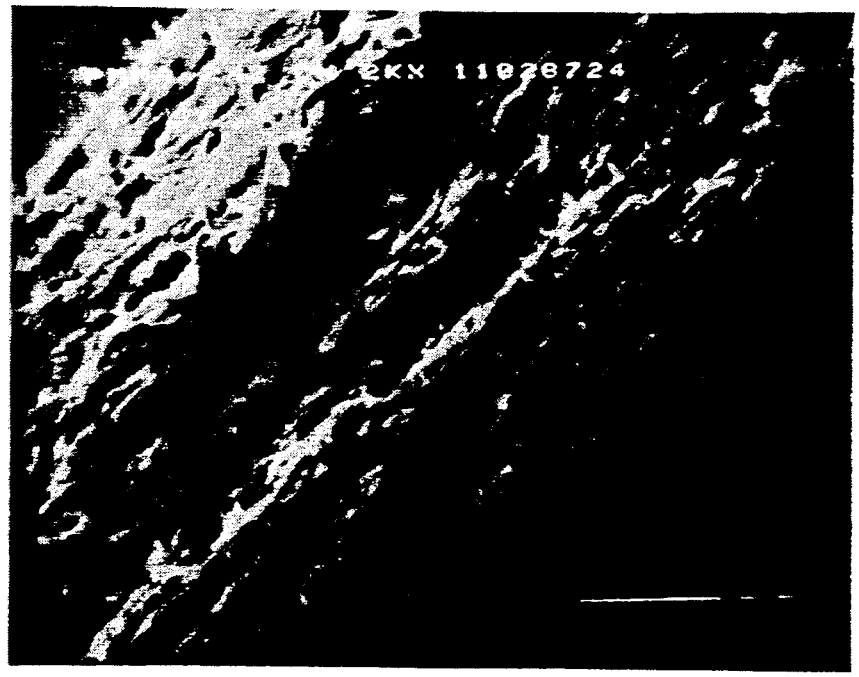
FIG. 18 is a scanning electron photomicrograph of the film of Example 39 at 2000×.

A photomicrograph of the unstretched film of Comparative Example C22 at 2000× magnification is shown in FIG. 17. Although this unstretched film has an open cell structure, the lack of airflow indicates that the cells are not connected by pores through the thickness of the film. A photomicrograph of the stretched film of Example 39 at 2000× magnification is shown in FIG. 18. This stretched film has ellipsoidal cells connected by pores. The pores are interconnected throughout the film as evidenced by the excellent Gurley value airflow of 137.1 sec/50 cc.

The various modifications and alterations of this invention will be apparent to those skilled in the art without departing from the scope and spirit of this invention and this invention should not be restricted to that set forth herein for illustrative purposes.

What is claimed is:

1. A method for preparing a microporous polymeric shaped article which comprises the steps of
   a) melt blending thermoplastic polymer with a solubilizing amount of a compatible liquid to form a homogeneous solution;
   b) forming a shaped article from the solution;
   c) cooling said shaped article at a rate and to a temperature sufficient to initiate thermodynamic, non-equilibrium liquid-liquid phase separation and then to solidify the thermoplastic polymer;
   d) stretching the article in a first direction sufficient to permanently attenuate the article and effect orientation of the polymer; and
   e) removing at least a substantial portion of the compatible liquid before or after said stretching step to form an oriented microporous shaped article.

2. The method of claim 1 wherein said homogeneous solution contains about 10 to 75 weight percent of said thermoplastic polymer in said compatible liquid.

3. The method of claim 1 wherein said thermoplastic polymer is polypropylene and said compatible liquid is tallowamine.

4. The method of claim 1 wherein said thermoplastic polymer is polyethylene and said compatible liquid is dioctyl phthalate.

5. The method of claim 1 wherein said solidified thermoplastic polymer is stretched at least 10 percent in at least one direction.

6. The method of claim 1 wherein said compatible liquid is removed by extraction or volatilization.

7. The method of claim 1 wherein said stretched article is further heated to a stabilizing temperature under restraint.

8. The method of claim 1 wherein said article is further stretched in a direction transverse to said first direction.

9. The method of claim 1 wherein said cooling comprises immersing said shaped article into a liquid cooling medium.

10. The method of claim 1 wherein said cooling comprises casting said shaped article onto a casting wheel.

11. The method according to claim 1 wherein said microporous polymeric shaped article has a thickness of more than zero and less than 1000 micrometers.

12. The method according to claim 1 wherein said microporous polymeric shaped articles has a matrix tensile strength at break in the oriented direction which is increased at least 10% over an unoriented article.

13. The method according to claim 1 wherein said article is stretched in the range of about 10 to 1000 percent to provide uniform, controlled porosity.

14. A method for preparing a microporous polymeric shaped article having a gradient porosity therethrough which comprises the steps of
   a) melt blending thermoplastic polymer with a solubilizing amount of a compatible liquid to form a homogeneous solution;
   b) forming a shaped article from the solution;
   c) rapidly cooling said shaped article from one surface thereof at a rate and to a temperature sufficient to initiate thermodynamic, non-equilibrium liquid-liquid phase separation and then to solidify the thermoplastic polymer;
   d) stretching the article in a first direction sufficient to permanently attenuate the article and effect orientation of the polymer; and
   e) removing at least substantial portion of the compatible liquid before or after said stretching step to form an oriented microporous shaped article having a gradient porosity therethrough.

* * * * *

UNITED STATES PATENT AND TRADEMARK OFFICE
CERTIFICATE OF CORRECTION

PATENT NO. : 5,238,618
DATED : August 24, 1993
INVENTOR(S) : Kevin E. Kinzer

It is certified that error appears in the above-indentified patent and that said Letters Patent is hereby corrected as shown below:

Col. 6, line 61     "of" should be -- or --

Col. 17, Table 8     last entry in column entitled "Stretch Temp (°C)" should read -- 138 -- instead of "128"

Signed and Sealed this

Thirty-first Day of May, 1994

Attest:

BRUCE LEHMAN

*Attesting Officer*     *Commissioner of Patents and Trademarks*